(12) United States Patent
Sharley et al.

(10) Patent No.: US 11,198,667 B2
(45) Date of Patent: Dec. 14, 2021

(54) CHEMICAL PROCESS OF PREPARING DEHYDROHEDIONE

(71) Applicant: International Flavors & Fragrances Inc., New York, NY (US)

(72) Inventors: James S. Sharley, Biggleswade (GB); Ian R. Baxendale, Durham (GB); Estela Espinos Ferri, Moncofar (ES); Ana Maria Collado Perez, Benicarlo (ES); Isabelle Fernandez Fernandez, Benicarlo (ES)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 16/499,626

(22) PCT Filed: Mar. 30, 2018

(86) PCT No.: PCT/US2018/025319
§ 371 (c)(1),
(2) Date: Sep. 30, 2019

(87) PCT Pub. No.: WO2018/183788
PCT Pub. Date: Oct. 4, 2018

(65) Prior Publication Data
US 2020/0039915 A1    Feb. 6, 2020

Related U.S. Application Data

(60) Provisional application No. 62/479,919, filed on Mar. 31, 2017.

(51) Int. Cl.
*C07C 67/307* (2006.01)
*C07C 67/317* (2006.01)
*C07C 69/738* (2006.01)

(52) U.S. Cl.
CPC .......... *C07C 67/307* (2013.01); *C07C 67/317* (2013.01); *C07C 69/738* (2013.01)

(58) Field of Classification Search
CPC ............................ C07C 67/307; C07C 69/738
USPC ........................................................ 560/126
See application file for complete search history.

(56) References Cited

U.S. PATENT DOCUMENTS

| | | | |
|---|---|---|---|
| 4,816,609 A * | 3/1989 | Harley | B01J 27/138 570/226 |
| 5,874,600 A | 2/1999 | Rautenstrauch et al. | |
| 6,586,620 B1 | 7/2003 | Crawford et al. | |
| 2009/0036692 A1* | 2/2009 | Shimizu | |
| 2016/0175829 A1 | 6/2016 | Bergens et al. | |

FOREIGN PATENT DOCUMENTS

| | | | |
|---|---|---|---|
| CN | 101302157 | * | 6/2008 |
| CN | 101302157 A | | 11/2008 |
| CN | 104086480 A | | 10/2014 |

OTHER PUBLICATIONS

Machine translation CN101302157 published 2008.*
March, Jerry(2001), Advanced Organic Chemistry: Reactions, Mechanisms, and Structure (5th ed.), New York: Wiley p. 1336-1337.*
Moussa, Sulfuryl Chloride: A Versatile Alternative to Chlorine. Australian Journal of Chemistry, Jan. 2012, 65 (1), 95-96.
Masilamani et al., Sulfuryl chloride as a reagent for selective chlorination of symmetrical ketones and phenols, J. Org. Chem., Oct. 1981, 46, 22, 4486-4489.
Warnhoff et al., 2-Chloro-2-Methylcyclohexanone and 2-Methyl-2-Cyclohexenone [(Cyclohexanone, 2-chloro-2-methyl-) and (2-Cyclohexen-1-one, 2-methyl-)], Org. Synth. 1957, 37, 8-12.
Demole et al., Synthèse du dihydrojasmonate de méthyle (pentyl-2-oxo-3-cyclopentylacétate de méthyle), Helv. Chim. Acta, Jan. 1962, 45, 2, 675-92.
Werkhoff et al., Methyl Dihydrojasmonate and its Stereoisomers: Sensory Properties and Enantioselective Analysis, Food Rev. Int., 2002, 18, 103-22.
Davies, Chem. World—UK, Feb. 2009, 40-44.
Mallia et al., The Use of Gases in Flow Synthesis, Org. Process Res. Dev. 20(2), 327-360, Aug. 2015.
Shono et al. Electroorganic chemistry, XXI. Selective Formation of α-Acetoxy Ketones and General Synthesis of 2,3-Disubstituted 2-Cyclopentenones through the Anodic Oxidation of Enol Acetates, J. Am. Chem. Soc., Oct. 1975, 97, 21, 6144-6147.
Ravid et al., New syntheses in dihydrojasmone series, J. Org. Chem. Aug. 1974, 39 (17), 2637-2639.
Winter et al., Further Explorations into the Synthesis of Dehydro-Hedione®, Helv. Chim. Acta, Feb. 2013, 96 (2), 246-258.
Shono et al., Electroorganic chemistry. 140. Electroreductively promoted intra- and intermolecular couplings of ketones with nitriles, J. Org. Chem., Dec. 1992, 57, 26, 7175-7187.
Shono et al., Electroreductive intramolecular coupling of γ- and δ-cyanoketones, Tetrahedron Lett., 1990, 31, 9, 1303-1306.
Kraft et al., Odds and Trends: Recent Developments in the Chemistry of Odorants, G. Angew. Chem. Int. Ed., Sep. 2000, 39, 17, 2980-3010.
Hu et al., Selective chlorination of aryl alkyl ketones by copper chloride, Chinese J. Appl. Chem. Feb. 2004, 21, 174-177.
Tilstam et al., Trichloroisocyanuric Acid: A Safe and Efficient Oxidant, Org. Process Res. Dev., Jun. 2002, 6, 4, 384-393.

(Continued)

*Primary Examiner* — Ana Z Muresan

(57) ABSTRACT

Disclosed is a chemical process of preparing dehydrohedione from Hedione via α-chlorination and elimination steps. The process can be conducted in a one-pot process or in a continuous reactor system. Accordingly, a simple and cost effective process of preparing cis-Hedione enriched products is developed through reduction of dehydrohedione in the presence of a chiral catalyst system.

14 Claims, 1 Drawing Sheet

(56) References Cited

OTHER PUBLICATIONS

Xu et al., α-Chlorination of Acetophenones Using 1,3-Dichloro-5,5-Dimethylhydantoin, Synth. Commun., Aug. 2006, 36, 2, 255-258.
Brummond et al., ChemInform Abstract: α-Chlorination of Ketones Using p-Toluenesulfonyl Chloride, Tetrahedron Lett., Mar. 1999, 40(12), 2231-2234.
Halland et al., Direct Organocatalytic Asymmetric α-Chlorination of Aldehydes, J. Am. Chem. Soc. Apr. 2004, 126(15), 4790-4791.
Schlama et al., Tetraethylammonium Trichloride: A Versatile Reagent for Chlorinations and Oxidations, Angew. Chem. Int. Ed. Nov. 1997, 36, No. 21, 2342-2344.
Guthrie et al., The chlorination of propiophenone; determination of pKa value and of the course of the reaction, Can. J. Chem., Nov. 1990, 68, 2060-2069.
Chapuis, C. et al. (2005) "Synthesis of cis-Hedione and Methyl Jasmonate via Cascade Baylis-Hillman Reaction and Claisen Ortho Ester Rearrangement," Helvetica Chimica Acta 88:3069-3085.
Crawford, K. et al. (2001) "A New Synthesis of Methyl 3-Oxo-3pentyl-I-cyclopentene-1-acetate," Synlett 7:1127-1128.
International Preliminary Report on Patentability in PCT/US2018/025319 dated Oct. 1, 2019.
International Search Report and Written Opinion in PCT/US2018/025319 dated Jul. 30, 2018.
Sharley, J. et al. (2016) "alpha, beta-Unsaturated ketones via copper (II) bromide mediated oxidation," Tetrahedron 72:2947-2954.

* cited by examiner

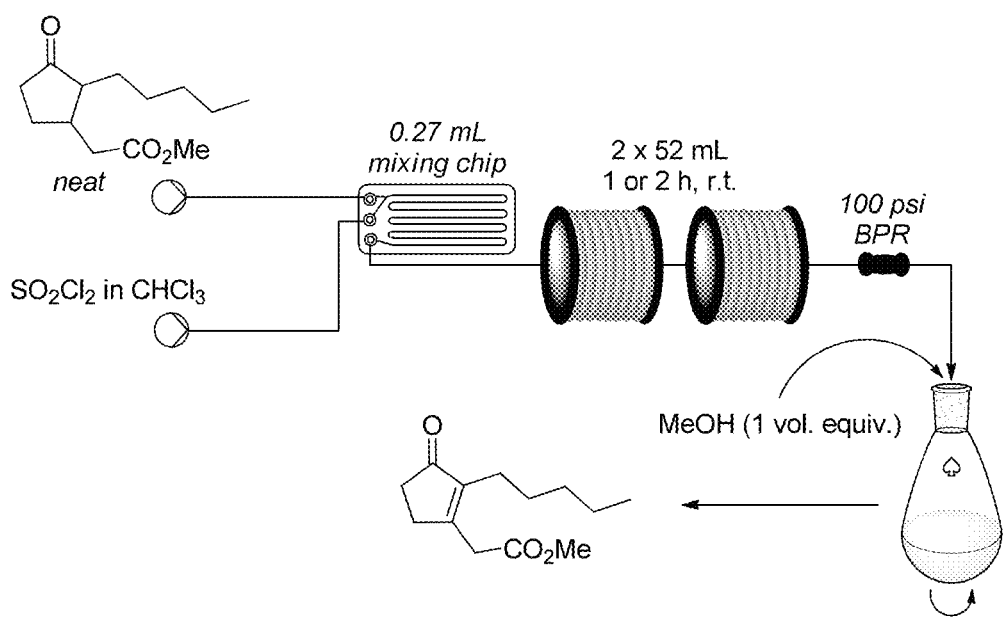

10

CHEMICAL PROCESS OF PREPARING DEHYDROHEDIONE

CROSS REFERENCE TO RELATED APPLICATIONS

This application is a national stage entry under 35 USC 371 for International Application No. PCT/US2018/025319, filed Mar. 30, 2018, which claims priority to U.S. Application No. 62/479,919, filed on Mar. 31, 2017. The contents of both applications are incorporated herein by reference in their entirety.

FIELD OF THE INVENTION

The present invention relates to synthesis of unsaturated cyclic ketones, in particular synthesis of dehydrohedione (DHH), a compound useful for preparing fragrance ingredient Hedione.

BACKGROUND OF THE INVENTION

Methyl 2-(3-oxo-2-pentylcyclopentyl)acetate (known as Hedione, also named as methyldihydrojasmonate) is a widely used synthetic fragrance ingredient produced at a scale of over 1,000 tons per year. Its unsaturated analogue, DHH, is a highly valuable synthetic target due to its ability to deliver Hedione diastereomeric mixtures comprising high (1R,2S)-(+)-cis isomer content through hydrogenation. Such mixtures possess a superior scent profile and hence are more valuable than commercial Hedione (90% trans). Although a wide variety of synthetic routes towards DHH have been developed, a preferred method of DHH synthesis at scale is simple oxidation of Hedione, which is cheap and readily available in its predominantly trans form (see U.S. Pat. No. 6,586,620). Synthesis of DHH from Hedione via an α-bromo intermediate has recently been reported (Sharley et al., *Tetrahedron* 2016, 72, 2947-2954). A process of oxidizing Hedione to DHH based on α-chlorination and elimination remains underexplored.

SUMMARY OF THE INVENTION

The present application discloses a new method of preparing dehydrohedione (DHH) from Hedione via α-chloro intermediate (α-chlorohedione). It is surprisingly found that DHH can be prepared in high yields via elimination of chlorine from α-chlorohedione and that the chlorinating step and the eliminating step can conveniently be performed in one pot or in a continuous reactor system.

In one aspect, the present invention provides a chemical process using methyl 2-(3-oxo-2-pentylcyclopentyl)acetate (Hedione) as a starting material and including the following steps: (a) chlorinating Hedione to obtain methyl 2-(2-chloro-3-oxo-2-pentylcyclopentyl)acetate (α-chlorohedione) in the presence of a chlorinating agent at a temperature of 55° C. or below, and (b) eliminating chlorine from α-chlorohedione to obtain methyl 2-(3-oxo-2-pentylcyclopent-1-en-1-yl)acetate (DHH).

In some embodiments, the chemical process of the present invention further including the step of reducing DHH to (1R,2S)-(+)-cis Hedione or its mixture in the presence of a chiral catalyst system.

Other aspects and advantages of the present invention can be better appreciated in view of the detailed description and claims.

BRIEF DESCRIPTION OF THE DRAWINGS

FIG. 1 shows an example schematic flow setup used for the $SO_2Cl_2$ oxidation of Hedione.

DETAILED DESCRIPTION OF THE INVENTION

The present invention is based on the surprising discovery of a facile process for chlorination-elimination oxidation of Hedione resulting in its formal oxidation to DHH. The process can be readily conducted in one pot or in a continuous reactor system. And accordingly, a simple and cost effective synthesis process of DHH from Hedione is developed.

In one aspect, Hedione is chlorinated to obtain α-chlorohedione in the presence of a chlorinating agent at a temperature of 55° C. or below, followed by eliminating chlorine from α-chlorohedione to obtain DHH.

In some embodiments, the eliminating step of α-chlorohedione can be conducted in a solvent comprising a lower alkyl alcohol, preferably methanol or ethanol, and more preferably, methanol. Lower alkyl amines and thiols are also suitable to promote the elimination reaction.

In some embodiments, the eliminating step, together with or without the chlorinating step, is conducted in methanol.

In some embodiments, the chlorinating agent is sulfuryl chloride, chlorine gas, a cyclic chlorine compound having a structural moiety of —N(Cl)—C(O)— (such as —C(O)—N(Cl)—C(O)—) in a 5- or 6-membered ring (such as 1,3-dichloro-5,5-dimethylhydantoin), or a combination thereof.

In one preferred embodiment, the cyclic chlorine compound is selected from the group consisting of trichloroisocyanuric acid, 1,3-dichloro-5,5-dimethylhydantoin, N-chlorosuccinimide, and combinations thereof.

In some embodiments, the chlorinating agent is added in portions into neat Hedione or a solution of Hedione.

In a preferred embodiment, the chlorinating step includes an initiation stage after the addition of a first portion of the chlorinating agent, and the initiation stage is achieved by a thermal initiation at a temperature of 40° C. or greater (preferably 40° C. to 120° C., and more preferably 45° C. to 55° C.) or a UV-visible light initiation, in the presence or absence of a radical initiator.

In one preferred embodiment, the chlorinating agent is added in the total amount of 0.8 to 2.2 chlorine equivalents relative to Hedione, and the first portion of the chlorinating agent constitutes 5% to 25% by weight of the total amount of the chlorinating agent added to the reaction.

In some embodiments, the chlorinating step is performed at a temperature of 30° C. or below (e.g., 0° C. to 30° C., 5° C. to 30° C., and 15° C. to 30° C.) after the initiation stage.

In some embodiments, the chlorinating agent is sulfuryl chloride ($SO_2Cl_2$). Sulfuryl chloride provides one chlorine atom when chlorinating Hedione, with the other chlorine atom forming a molecule of HCl as a by-product. As such, one mole of sulfuryl chloride equals to one chlorine equivalent in the chlorination reaction relative to one mole of Hedione.

In some embodiments, when the chlorinating agent is sulfuryl chloride, the chlorinating step is performed at a temperature of 30° C. or below without a solvent or in a solvent selected from the group consisting of chloroform, dichloromethane, ethyl acetate, toluene, xylenes, and combinations thereof. In one preferred embodiment, the amount of sulfuryl chloride is in a range of 0.75 to 1.1 chlorine equivalents as compared to that of Hedione.

In some embodiments, the chemical process further comprising reducing DHH to (1R,2S)-(+)-cis Hedione or its mixture in the presence of a chiral catalyst system.

Exemplary chiral catalysts include ruthenium (II) catalyst comprising ligands formed of bidentate phosphines, characterized in that it is obtainable by a process which comprises treating an appropriate Ru(II) complex and a bidentate diphosphine ligand, present in equimolar amounts, with an acid of formula HX, wherein X is a non-coordinating anion, said acid being used in a ratio which does not exceed 2 molar equivalents per mole of the Ru(II) complex, the treatment being carried out in a non-coordinating or weakly coordinating medium and under an inert atmosphere. See U.S. Pat. No. 5,874,600. Suitable Ru(II) complexes can be selected from the group of Ru(II) compounds of the type (diene)Ru(allyl)$_2$ or bis(pentadienyl)Ru such as bis(2-methallyl) (1,5-cyclooctadiene)Ru(II), bis(2,4-dimethylpentadienyl)Ru(II) or bis(2,4-dimethyl-1-oxapentadienyl)Ru(II). The diphosphine ligand can be the chiral ligands known under the abbreviations of Me-DuPHOS, Et-DuPHOS, BINAP, TolBINAP, SKEWPHOS and JOSIPHOS, preferably (R,R)-(−)-Me-DuPHOS.

In some embodiments, the chlorinating and eliminating steps are performed in a one-pot process. In some embodiments, the chlorinating step, the eliminating step, or both are performed in a continuous reactor system.

In one preferred embodiment, the continuous reactor system is a single continuous stirred tank reactor ("CSTR"), a system having multiple CSTRs in series, or a continuous flow reactor system such as a tubular flow system. In any continuous reactor system, Hedione and the chlorinating agent can be fed into the system which is pressurized using a back pressure regulator (BPR).

Combinations of any of the embodiments disclosed herein are possible and contemplated.

The term "lower alkyl alcohol", as used herein, means an alcohol of formula "R—OH", where R is a lower alkyl group containing 1 to 4 carbon atoms. Representative examples of lower alkyl alcohol include, but are not limited to, methanol, ethanol, n-propanol, iso-propanol, etc., preferably methanol and ethanol, and more preferably methanol.

The term "chlorine equivalent", as used herein, refers to the molar equivalent of chlorine atoms supplied by the chlorinating agent in the chlorination reaction relative to Hedione.

The term "flow reactor", as used herein, refers to a dynamic reactor system in which reactants flow continuously into the vessel and products are continuously removed, in contrast to a batch reactor (as defined in McGraw-Hill Dictionary of Scientific & Technical Terms, 6E, Copyright® 2003 by The McGraw-Hill Companies, Inc.). Examples of flow reactors include, but are not limited to, continuous flow microreactors (e.g., the H-Cube® continuous flow hydrogenation reactor marketed by ThalesNano), fluidized bed reactors, membrane reactors, laminar flow reactors, baffle flow reactors and the like.

The singular forms "a", "an", and "the", as used herein, include plural reference, and vice versa, unless the context clearly dictates otherwise.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

In one aspect, the present invention particularly relates to a chemical process involving the transformation of Hedione to DHH. Of all the possible isomers of Hedione in Scheme 1, the (1R,2S)-(+)-cis isomer is the most desirable, being almost entirely responsible for the characteristic odor of Hedione. Whilst enantioselective routes to this compound have been reported, they are prohibitively expensive and poorly scalable, hence, 'cis-enhancement' of Hedione® is still the favored approach within the fragrance industry. This is primarily achieved through hydrogenation of DHH (1b, its α,β-unsaturated analogue). Although several syntheses of DHH have been developed, the preferred method of DHH synthesis on a large scale still remains through direct oxidation of Hedione (see, e.g., U.S. Pat. No. 6,586,620).

Scheme 1. Hedione (1) diastereomers and the "cis-enhancement" process

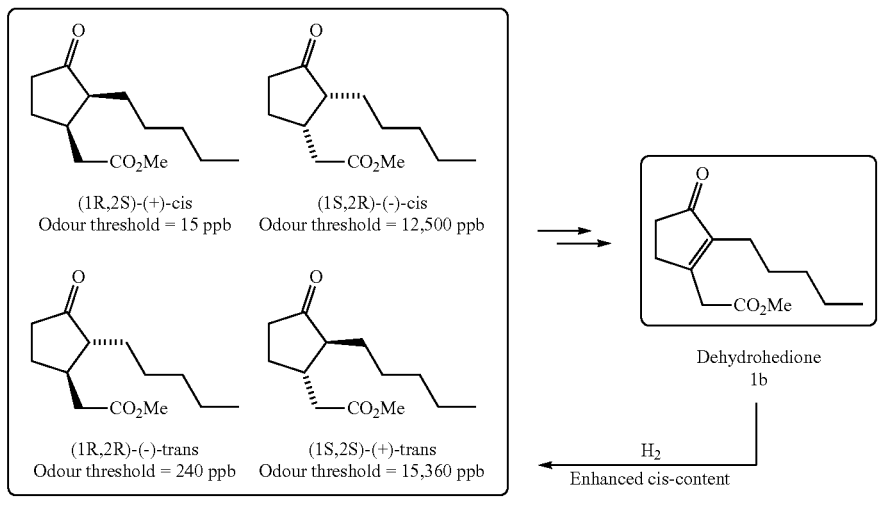

Hedione
1

Herein, one advantage of this process involves a convenient and operationally simple means of effecting the oxidative transformation of Hedione 1 to DHH 2 via α-chlorohedione 5, as shown in Scheme 2.

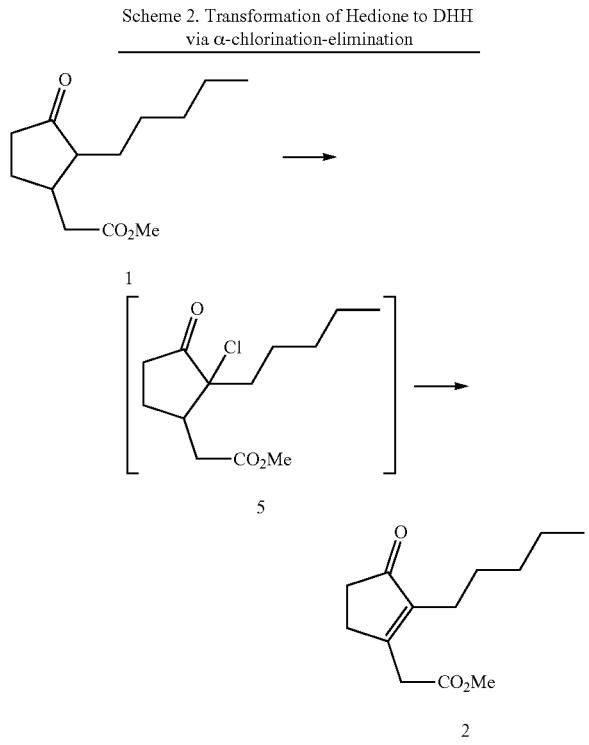

Scheme 2. Transformation of Hedione to DHH via α-chlorination-elimination

Suitable chlorinating agents include sulfuryl chloride ($SO_2Cl_2$), chlorine gas, and cyclic chlorine compounds each having a structural moiety of —N(Cl)—C(O)— in a 5- or 6-membered ring. These chlorinating agents are cost effective and readily available. They surprisingly chlorinate Hedione in high yields and under mild conditions.

Exemplary cyclic chlorine compounds having a structural moiety of —N(Cl)—C(O)— in a 5- or 6-membered ring include trichloroisocyanuric acid (TCCA, 6) and its salts (such as a sodium salt), dichloroisocyanuric acid and its salts (such as a sodium salt), monochloroisocyanuric acid and its salts (such as a sodium salt), 1,3-dichloro-5,5-dimethylhydantoin (DCDMH, 7), and N-chlorosuccinimide (NCS, 8), whose structural formulae are shown in Scheme 3 below. TCCA has three chlorine atoms available for a chlorination reaction. As such, 1 mole of TCCA (including its salts) equals to 3 chlorine equivalents relative to 1 mole of Hedione. Similarly, 1 mole of dichloroisocyanuric acid (including its salts) equals to 2 chlorine equivalents relative to 1 mole of Hedione, 1 mole of monochloroisocyanuric acid (including its salts) equals to a chlorine equivalent relative to 1 mole of Hedione, 1 mole of DCDMH equals to 2 chlorine equivalents relative to 1 mole of Hedione and 1 mole of NCS equals to 1 chlorine equivalent relative to 1 mole of Hedione.

Among these cyclic chlorine compounds, TCCA 6, an inexpensive industrial disinfectant and bleaching agent used in swimming pools and in the textile industry, is preferable for its selectivity towards the desired α-position (5) chlorination.

Scheme 3. Structural formulae of TCCA 6, DCDMH 7 and NCS 8

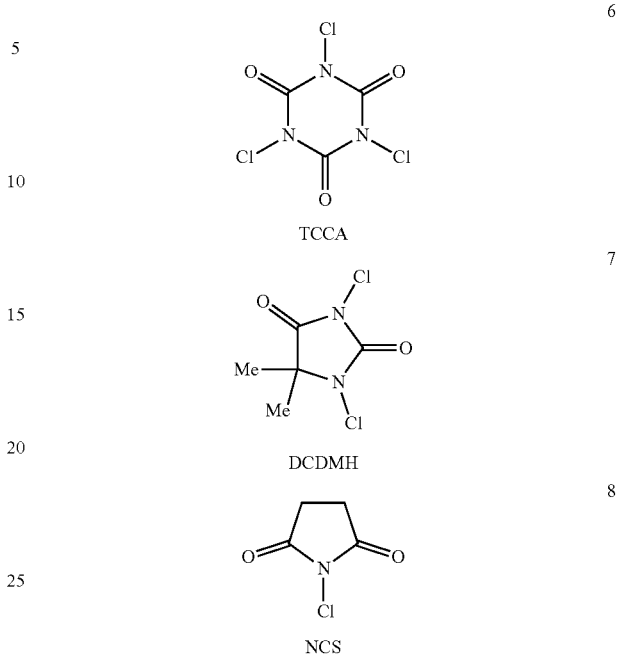

Another advantage of this process comes with the subsequent straightforward elimination of chlorine from α-chlorohedione to obtain DHH. More advantageously, the chlorine elimination in many cases occurs spontaneously when the chlorination reaction is conducted in a lower alkyl alcohol, especially in methanol. This is a surprising finding, as the spontaneous elimination of chlorine from the α-chlorohedione 5 is unprecedented. While not intending to be bound by theory, the system described in Scheme 4 is proposed as a mechanistic pathway, in which methanol involves in the elimination of α-chloro and the formation of ethylenic bond.

Scheme 4: Proposed chlorination-elimination sequence

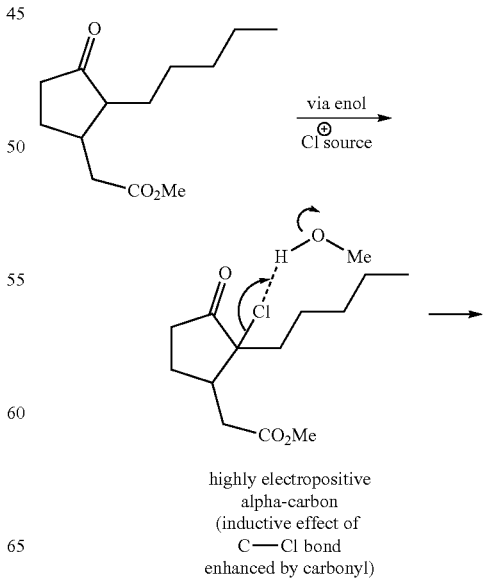

highly electropositive
alpha-carbon
(inductive effect of
C—Cl bond
enhanced by carbonyl)

-continued

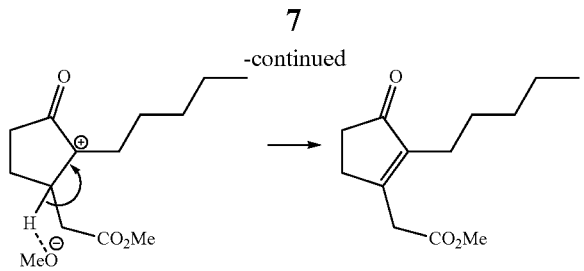

The chlorinating step is preferably conducted at a temperature of 55° C. or below, so as to avoid a runaway reaction. More preferably, the reaction temperature in the chlorinating step is kept at 30° C. or below, and even more preferably, at an ambient temperature such as from 15° C. to 25° C. In some embodiments, the chlorinating agent is added portion-wise. For example, the chlorinating agent alone or in a solution (e.g. a methanol solution) is added in portions into neat Hedione or a solution of Hedione. In some embodiments, the chlorinating agent is added at a total amount of 0.8 to 2.2 chlorine equivalents relative to Hedione. A slight superstoichiometric chlorine equivalent of the chlorinating agent, for instance, from 1 to 1.5 chlorine equivalents for the cyclic chlorine compound and 0.7 to 1.5 chlorine equivalents for $SO_2Cl_2$, is preferable for the conversion to α-chlorohedione.

When a cyclic chlorine compound is used as a chlorinating agent, an initiation stage is beneficial after the addition of a first portion of the chlorinating agent.

Table 1 below shows the chlorination results using TCCA. Typically, solid TCCA was added in portions to control the temperature and avoid a runaway reaction. At a high temperature such as 64.7° C. (Table 1, entry 1), the reaction occurred immediately upon addition of the TCCA which makes controlling the reaction temperature challenging. At a low temperature (e.g., 30° C., 25° C., and 15° C.), a delay was observed between addition of TCCA and reaction initiation. Not to be bound by any theory, it is believed that TCCA itself is not reacting directly with the starting material (as an electrophilic chlorinating agent) but that it acts as a source of $Cl_2$ or Cl radicals which are the reactive species.

TABLE 1

Chlorination reaction of Hedione with TCCA

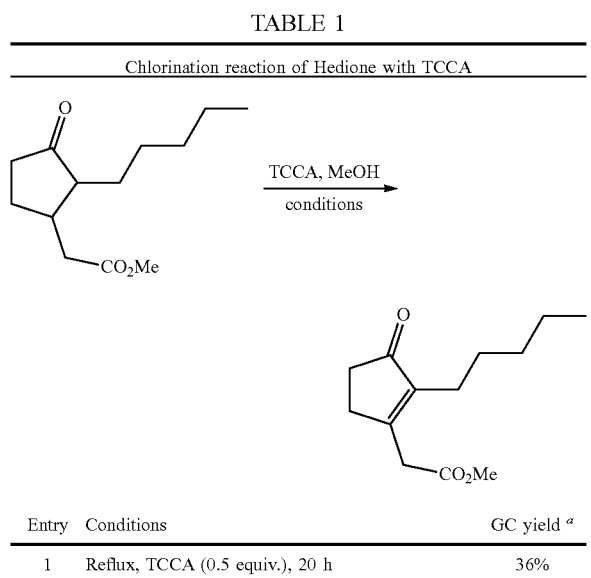

| Entry | Conditions | GC yield [a] |
|---|---|---|
| 1 | Reflux, TCCA (0.5 equiv.), 20 h | 36% |
| 2 | Thermal initiation → <30° C., TCCA (0.5 equiv.), HCl (2 drops), 20 h | 48% |

TABLE 1-continued

Chlorination reaction of Hedione with TCCA

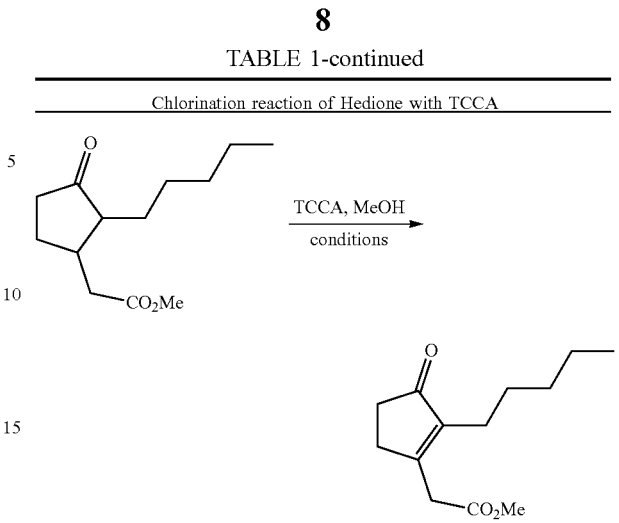

| Entry | Conditions | GC yield [a] |
|---|---|---|
| 3 | Thermal initiation → <30° C., TCCA (0.5 equiv.), HCl (5 drops), 20 h | 35% |
| 4 | Thermal initiation → <30° C., TCCA (0.5 equiv.), $SiO_2SO_3H$ (0.5 g), 20 h | 47% |
| 5 | Thermal initiation → <30° C., TCCA (0.5 equiv.), 20 h | 56% |
| 6 | Thermal initiation → <30° C., TCCA (0.33 equiv.), 20 h | 51% |
| 7 | Thermal initiation → <30° C., TCCA (0.67 equiv.), 20 h | 54% [b] |

Reactions conducted with 1M Hedione in methanol).
[a] Calculated using n-undecane as an internal GC standard.
[b] Product isolated by Silica column chromatography.

An initiation stage assists cleavage of an N—Cl bond in TCCA to generate a chlorine radical or $Cl_2$ with an initiation stage using radical initiators such as AIBN. This is classically achieved by heating or irradiating with UV-visible light. By heating the reaction therefore, this initiation can be induced and made to occur predictably. The initiation is highly exothermic and leads to a rapid propagation in the presence of additional TCCA. Initiating the reaction in the presence of small amounts of TCCA and then dosing the remainder of the TCCA afterwards is a preferred way to carry out the process. Thermal initiation typically occurs at 45° C. to 51° C. It is also possible to initiate the reaction by irradiation with UV-visible light, as demonstrated for the chlorination of chloro(methyl)pyridine with TCCA in Wen et al., CN 104086480 A. Interestingly, the reaction can proceed smoothly and initiate at the above temperature in the presence of a radical scavenger ($Na_2SeO_3$).

By performing the reaction at reflux, a lower selectivity and yield were observed (see Table 1, entry 1). The reaction was heated briefly in the presence of 5% TCCA (by mole of Hedione) to induce initiation and then cooled intermittently while the remainder of the TCCA was added. In the presence of catalytic acid, the rate of the reaction was enhanced, however, with less selectivity or poorer yields (see Table 1, entries 2 and 3). The addition of acid did not lead to initiation of the reaction. TCCA stoichiometry could be brought down to 0.33 equivalents (approximate 1 chlorine equivalent) without a drastic impact on yield (Table 1, entries 5 and 6) and using more than 0.67 equivalents (2 chlorine equivalents) resulted in a good yield (Table 1, entry 7).

Similar phenomenon was also observed with the use of other cyclic chlorine compounds such as NCS and DCDMH, and $Cl_2$ gas. Among others, an initiation stage at 45° C. to 55° C. is preferred after the addition of a first portion of the chlorinating agent, which constitutes 5 to 25% by weight of the total amount of the chlorinating agent. The chlorinating step after the initiation stage, however, is preferably performed at a temperature of 30° C. or below.

Table 2 below shows yields of α-chlorohedione were obtained by using different chlorinating agents.

The use of sulfuryl chloride ($SO_2Cl_2$) resulted in high yields (Table 2, entry 5). The reaction with $SO_2Cl_2$ was conducted in chloroform for 5 hours at 25° C. followed by the addition of methanol for eliminating chlorine from the resultant α-chlorohedione, thereby obtaining DHH.

TABLE 2

Yields using different chlorinating agents

| Entry | Reagent | GC yield [a] |
|---|---|---|
| 1 | TCCA | 56% |
| 2 | NCS | 48% |
| 3 | DCDMH | 35% |
| 4 | $Cl_2$ gas | 20% |
| 5 | $SO_2Cl_2$ | 75% [b] |

Reactions conducted on a 50 mmol scale (1M).
[a] Calculated using n-undecane as an internal GC standard.
[b] conducted as a two-step process, $SO_2Cl_2$ added in $CHCl_3$ followed by addition of MeOH after 5 hours.

The $SO_2Cl_2$ chlorination step can be carried out in suitable solvents as shown in Table 3. Conducting the reaction under a solvent-free condition led to a yield of 58% (Table 3, entry 4). Methanol was added to the reaction mixture after the chlorination step.

TABLE 3

Chlorination of Hedione with $SO_2Cl_2$ in different solvents

TABLE 3-continued

| Entry | Solvent | $^1$H-NMR yield [a] |
|---|---|---|
| 1 | $CHCl_3$ | 73% |
| 2 | EtOAc | 72% |
| 3 | Toluene | 74% |
| 4 | Neat | 58% |

Reactions conducted on a 5 mmol scale (1M).
[a] Calculated using 1,3,5-trimethoxybenzene as an external $^1$H-NMR standard.

Unlike the cyclic chlorine compounds and $Cl_2$ gas, 'initiation' is not necessary for the reaction with $SO_2Cl_2$. The chlorination reaction occurs upon mixing Hedione and $SOCl_2$ between 0° C. and 25° C. It is likely that $SO_2Cl_2$ reacts directly with the enolized Hedione, acting as an electrophilic chlorinating agent.

Gradual addition of $SO_2Cl_2$ is preferred to keep the temperature at 30° C. or below. Cooling means during $SO_2Cl_2$ addition can be used in a large-scale reaction. The stoichiometry of $SO_2Cl_2$ between 0.5 equivalents (also 0.5 chlorine equivalents) and 1.1 equivalents is suitable to achieve a high yield (Table 4). Typically, the reaction is performed with Hedione at a concentration of up to 5 moles/Liter ("M"), e.g., up to 3 M, 0.01 M to 5 M with an upper limit of 5 M, 4 M, 3 M, and 2 M and a lower limit of 0.01 M, 0.05 M, 0.1 M, 0.5 M, and 1 M, and preferably at 1 M to 2 M. The chlorination step can be complete within 10 hours (such as within 8 hours, within 5 hours, within 3 hours, within 2 hours, 1 hour to 10 hours). The elimination step can be complete within 24 hours (e.g., within 20 hours, within 16 hours, within 12 hours, within 10 hours, within 8 hours, within 5 hours, within 3 hours, and 1 hour to 24 hours). The reactions can be monitored with a liquid chromatography and mass spectrometer (LC-MS) showing the peaks of Hedione, α-chlorohedione (the intermediates), and DHH (the final product).

Table 4 below shows the chlorination of Hedione to α-chlorohedione and the subsequent elimination to DHH. The yield is calculated as the overall yield from Hedione to DHH.

TABLE 4

Preparing DHH using $SO_2Cl_2$ and Hedione

| Entry | $SO_2Cl_2$ equiv. | Yield |
|---|---|---|
| 1 | 0.5 | 48% [a] |
| 2 | 0.75 | 72% [a] |

TABLE 4-continued

| 3 | 1.0 | 75% [a] |
|---|-----|---------|
| 4 | 1.1 | 77% [b] |

Reactions conducted in a 1M Hedione solution.
[a] Calculated using n-undecane as an internal GC standard.
[b] Isolated yield-reaction conducted in a 2M Hedione solution and product isolated by distillation.

While $SO_2Cl_2$ has been used as an α-chlorinating agent (Moussa, *Aust. J. Chem.* 2012, 65, 95-96; Masilamani et al., *J. Org. Chem.* 1981, 46, 4486-4489), its use in a one-pot chlorination-elimination process is novel. $SO_2Cl_2$ was used for the synthesis of a completely different compound, 2-methyl-2-cyclohexenone from 2-methylcyclohexanone as demonstrated (Warnhoff et al., *Org. Synth.* 1957, 37, 8-12). However, this was performed as a discrete 2-step procedure wherein $CCl_4$ was used as a solvent for the initial chlorination and either collidine or a LiCl/DMF system was used to promote elimination in a completely separate reaction of a fully worked up α-chloro product. The fact that $SO_2Cl_2$ is liquid makes the process using $SO_2Cl_2$ highly attractive in terms of transposition into a continuous-flow process. Another advantage is that no precipitates are formed during the reaction with $SO_2Cl_2$.

Upon the formation of DHH, the chemical process of the present invention may further comprise a step of reducing DHH to (1R,2S)-(+)-cis Hedione or its mixture. The reducing step can be performed using hydrogen in the presence of a chiral catalyst system. See Demole et al., *Helv. Chim. Acta* 1962, 45, 675-92; Werkhoff et al., *Food Rev. Int.* 2002, 18, 103-22; and Davies, *Chem. World-UK* 2009, February, 40-44.

This application also discloses a system for conducting the chemical process of the present invention. By virtue of the spontaneous elimination of chlorine from α-chlorohedione, the oxidation of Hedione to DHH via chlorinating and eliminating steps, as well as the subsequent reduction of DHH to (1R,2S)-(+)-cis Hedione, may be performed in a one-pot process, which greatly simplifies the process and the equipment required.

Instead of the use of a batch reactor, the chlorinating step, the elimination step, or both may be performed in a continuous reactor system. The continuous reactor system employed in the present invention may comprise a single continuous stirred tank reactor ("CSTR"), a system having multiple CSTRs in series, or a continuous flow reactor system, such as H-Cube® continuous flow hydrogenation reactor marketed by ThalesNano. Some examples of continuous flow reactor system are shown in US20160175829.

A continuous flow reactor system is attractive for the reaction with $SO_2Cl_2$, due to the fact that $SO_2$ gas evolution occurs. In batch, exothermic reactions that involve the generation of gas are prone to rapid gas evolution and overpressures, hence, very careful addition of reagents to such reactions are necessary at scale. Gas generation can be easily managed in flow by pressurizing the system with a suitable back pressure regulator (BPR) (Mallia et al., *Org. Process Res. Dev.* 2015). The gas can be kept in solution whilst in the flow stream and then removed from the reaction upon passing the BPR. This allows for steady, constant removal of gas in a manner that carries with it improved safety implications compared to batch. Another advantage of continuous flow reactor system for the reaction with $SO_2Cl_2$ is that all materials used are miscible liquids.

FIG. 1 shows a schematic semi-continuous system of the present invention, in which the chlorination step is performed in flow and the elimination is performed batch-wise.

As an illustrative example, neat Hedione was fed into a 0.27 mL Uniqsis mixing chip along with a solution of $SO_2Cl_2$ in $CHCl_3$ at a rate such that 1.1 equivalent of $SO_2Cl_2$ was used with a residence time of 1 hour to 2 hours within the flow reactors. The flow system was pressurized using a 100 psi (~7 bar) BPR for the chlorination step and the outlet was collected in a stirred flask. Upon halting collection, methanol (MeOH) was added and the reaction was left to stir for 16 hours at 25° C. The system worked well and gave comparable yields to the batch process (Table 5 vs. Table 4). Improved heat dissipation or transfer meant that the exotherm was well controlled and the release of $SO_2$ gas was steady and controlled upon the stream passing the BPR. A 100 psi BPR was sufficient to keep all gas in solution within the reactor.

TABLE 5

Oxidation of Hedione with $SO_2Cl_2$ in flow $SO_2Cl_2$ (1.1 equiv.)
flow
$CHCl_3$, r.t., 1-2 h,
then MeOH, r.t., O/N

| Entry | $SO_2Cl_2$ conc. (M) | Hedione conc. (M) | time (h)[a] | Yield |
|-------|----------------------|-------------------|-------------|-------|
| 1 | 1 | 0.76 | 1 | 74 [b] |
| 2 | 1 | 0.76 | 2 | 78 [b] |
| 3 | 3 | 1.69 | 1 | 67 [b] |
| 4 | 6 | 2.45 | 1 | 60 [b] |
| 5 | 1.45 | 1 | 1 | 72 [c] |

Reactions conducted on a 5 mmol scale (1M).
[a] Residence time for first step.
[b] Calculated using n-undecane as an internal GC standard.
[c] Isolated yield of 35 min. sample collection-product isolated by $SiO_2$ column chromatography.

It is possible to perform the second step (MeOH addition) in a flow reactor that is united with the first step flow units to create a single linked processing stream.

As presented a new chemical process for the oxidation of Hedione to DHH has been developed that offers significant advantages over prior work in terms of cost-effectiveness and potential for continuous manufacture. The oxidation reaction with chlorinating agents such as TCCA or $SO_2Cl_2$ can be conveniently performed in a one-pot process through chlorination and elimination. This oxidation reaction can be readily operated as a flow process.

EXAMPLES

General Method

Unless otherwise stated, all solvents were purchased from Fisher Scientific (Hampton, N.H.) and used without further purification. Substrates and their precursors and reagents were purchased from Alfa Aesar (Haverhill, Mass.) or Sigma Aldrich (St. Louis, Mo.) and used as received.

$^1$H-NMR spectra were recorded on either Bruker Avance-400 or Varian VNMRS-700 instruments and are reported relative to residual solvent: $CHCl_3$ (δ 7.26 ppm). $^{13}$C-NMR spectra were recorded on the same instruments and are reported relative to $CHCl_3$ (δ 77.16 ppm). Data for $^1$H-NMR are reported as follows: chemical shift (δ/ppm) (multiplicity, coupling constant (Hz), integration). Multiplicities are reported as follows: s=singlet, d=doublet, t=triplet, q=quartet, p=pentet, m=multiplet, br. s=broad singlet, app.=apparent. Data for $^{13}$C-NMR are reported in terms of chemical shift (δc/ppm). DEPT-135, COSY, HSQC, HMBC and NOESY experiments were used in structural assignments.

IR spectra were obtained using a Perkin Elmer Spectrum Two UATR Two FT-IR Spectrometer (neat, ATR sampling) with the intensities of the characteristic signals being reported as weak (w, <20% of tallest signal), medium (m, 21-70% of tallest signal) or strong (s, >71% of tallest signal). Low and high resolution mass spectrometry was performed using the indicated techniques. Gas chromatography mass spectrometry (GC-MS) was performed on a Shimadzu QP2010-Ultra equipped with an Rxi-5Si1 MS column in EI mode.

Example 1. Synthesis of Dehydrohedione (DHH) by TCCA Oxidation of Hedione

Hedione (11.3 g, 50 mmol) was dissolved in MeOH (40 mL) and mixed with trichloroisocyanuric acid (TCCA), (0.58 g, 5 mol %). The mixture was stirred and heated to 50° C. in order to initiate the reaction. After initiation, the reaction was brought back to room temperature (i.e., 25° C.) and the remainder of the TCCA (5.23 g, 45 mol %) was added over 10 min, keeping the temperature below 30° C. The reaction was then left to stir at room temperature for 20 hours before the resultant suspension was filtered and the filtrate was concentrated in vacuo. The residue was purified using silica column chromatography (8:2, hexane:EtOAc) to give DHH as a colorless liquid (5.83 g, 52%).

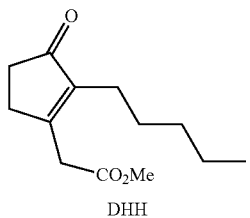

DHH

Chemical Formula: $C_{13}H_{20}O_3$
Molecular Weight: 224.30

$^1$H NMR (400 MHz, $CDCl_3$) δ 3.74 (s, 3H), 3.46 (s, 2H), 2.63 (m, 2H), 2.42 (m, 2H), 2.19 (m, 2H), 1.21-1.44 (m, 6H), 0.88 (t, J=8.0 Hz, 3H) ppm; $^{13}$C NMR (100 MHz, $CDCl_3$) δc 209.2, 169.6, 163.3, 143.3, 52.3, 36.6, 34.3, 31.8, 29.7, 28.0, 23.2, 22.5, 14.0 ppm; FT-IR $v_{max}$ 1171 (s), 1194 (s), 1435 (m), 1644 (m), 1698 (s), 1738 (s), 2860 (w), 2929 (w), 2954 (w) $cm^{-1}$; GC-MS $R_t$ 4.70 min, m/z 224 $[M]^+$, 193 $[M-OMe]^+$, 154 $[M-C_5H_{11}]^+$, 151 $[M-CH_2CO_2Me]^+$.

Example 2. Batch Synthesis of DHH by $SO_2Cl_2$ Oxidation of Hedione

Hedione (113 g, 0.5 mol) was dissolved in $CHCl_3$ (110 mL). Sulfuryl chloride (40.4 mL, 1.1 equiv.) was added slowly, keeping the reaction below 30° C. The reaction mixture was left to stir at room temperature for 2 hours before MeOH (100 mL) was added. The resultant mixture was then stirred for 3 hours before solvents were removed under reduced pressure. To the residue, a saturated aqueous $Na_2CO_3$ solution (200 mL) was added. Subsequently, the mixture was stirred for 16 hours at room temperature before the product was extracted with EtOAc (2×200 mL). After concentration of the organic layers in vacuo the resultant liquid was purified using vacuum distillation (1 mbar, 100-110° C.) to give DHH as a colorless liquid (86.2 g, 77%).

Example 3. Flow Synthesis of DHH by $SO_2Cl_2$ Oxidation of Hedione

A solution of $SO_2Cl_2$ (1.45 M in $CHCl_3$) and neat Hedione were directed into a Uniqsis 0.27 mL mixing chip at 0.682 mL/min and 0.201 mL/min respectively where they were merged. The outlet of the mixing chip was directed into a 52 mL reactor coil at room temperature (Retention time $R_t$=1 hour) and collected in a stirred round-bottom flask (collection time=8 hours). A sample was collected separately 35 minutes since Hedione and $SO_2Cl_2$ were fed into the system. Upon halting collection, MeOH (7 mL) was added and the mixture was stirred at room temperature for 16 hours. The solvents were removed in vacuo and a saturated aqueous $Na_2CO_3$ solution (20 mL) was added to the residue. The mixture was then stirred for 20 hours at room temperature. The product was extracted with EtOAc (2×20 mL). After concentration of the organic layers in vacuo the resultant liquid was purified using silica column chromatography (8:2, hexane:EtOAc) to give DHH as a colorless liquid (5.06 g, 72%).

All references cited herein are incorporated by reference in their entirety. The foregoing examples and description of certain preferred embodiments should be taken as illustrating, rather than as limiting, the present invention. As would be readily appreciated by a person skilled in the art, numerous variations and combinations of the features set forth above can be utilized without departing from the present invention, which are all encompassed by the present invention.

What is claimed is:

1. A chemical process comprising:
    chlorinating methyl 2-(3-oxo-2-pentylcyclopentyl)acetate to obtain methyl 2-(2-chloro-3-oxo-2-pentylcyclopentyl)acetate ("α-chlorohedione") in the presence of a chlorinating agent at a temperature of 55° C. or below, and
    eliminating chlorine spontaneously from α-chlorohedione to obtain methyl 2-(3-oxo-2-pentylcyclopent-1-en-1-yl)acetate ("dehydrohedione") in the presence of methanol at a temperature of less than 30° C.

2. The process of claim 1, wherein the chlorinating agent is sulfuryl chloride, chlorine gas, a cyclic chlorine compound having a structural moiety of —C(O)—N(Cl)—C(O)— in a 5- or 6-membered ring, or a combination thereof.

3. The process of claim 2, wherein the cyclic chlorine compound is selected from the group consisting of trichloroisocyanuric acid, 1,3-dichloro-5,5-dimethylhydantoin, N-chlorosuccinimide, and combinations thereof.

4. The process of claim 1, wherein the chlorinating agent is added in portions into a solution of methyl 2-(3-oxo-2-pentylcyclopentyl)acetate.

5. The process of claim 4, wherein the chlorinating step includes an initiation stage after the addition of a first portion of the chlorinating agent, and the initiation stage is achieved by a thermal initiation at a temperature of 45 to 55° C. or a UV-visible light initiation, in the presence or absence of a radical initiator.

6. The process of claim 5, wherein the chlorinating agent is added in the total amount of 0.8 to 2.2 chlorine equivalents relative to methyl 2-(3-oxo-2-pentylcyclopentyl)acetate, and the first portion of the chlorinating agent constitutes 5 to 25% by weight of the total amount of the chlorinating agent.

7. The process of claim 1, wherein the chlorinating step is performed at a temperature of 30° C. or below after an initiation stage.

8. The process of claim 2, wherein the chlorinating agent is sulfuryl chloride.

9. The process of claim 8, wherein the chlorinating step is performed at a temperature of 30° C. or below in a solvent selected from the group consisting of dichloromethane, chloroform, acetonitrile, ethyl acetate, toluene, xylenes, and combinations thereof.

10. The process of claim 8, wherein the amount of sulfuryl chloride is in a range of 0.75 to 1.1 molar equivalents as compared to that of methyl 2-(3-oxo-2-pentylcyclopentyl) acetate.

11. The process of claim 1, further comprising reducing dehydrohedione to (1R,2S)-(+)-cis methyl 2-(3-oxo-2-pentylcyclopentyl)acetate or its mixture in the presence of a chiral catalyst.

12. The process of claim 1, wherein the chlorinating and eliminating steps are performed in one pot.

13. The process of claim 1, wherein the chlorinating step, the elimination step, or both are performed in a continuous reactor system.

14. The process of claim 13, wherein the continuous reactor system is a single continuous stirred tank reactor ("CSTR"), a system having multiple CSTRs in series, or a continuous flow reactor system, and methyl 2-(3-oxo-2-pentylcyclopentyl)acetate and the chlorinating agent are fed into the continuous reactor system which is pressurized using a back pressure regulator (BPR).

* * * * *